United States Patent [19]

Pollak et al.

[11] Patent Number: 5,287,169
[45] Date of Patent: Feb. 15, 1994

[54] CONTRACTLESS MODE OF ELECTROREFLECTANCE

[75] Inventors: Fred H. Pollak, New York; Xiaoming Yin, Brooklyn, both of N.Y.

[73] Assignee: Brooklyn College Research and Development Foundation, Brooklyn, N.Y.

[21] Appl. No.: 861,104

[22] Filed: Mar. 31, 1992

Related U.S. Application Data

[63] Continuation-in-part of Ser. No. 695,019, May 3, 1991, abandoned.

[51] Int. Cl.[5] .......................................... G01N 21/55
[52] U.S. Cl. .................................. 356/445; 356/432; 250/226
[58] Field of Search ................. 356/432, 432 T, 445; 250/226, 571; 204/290 R

[56] References Cited

U.S. PATENT DOCUMENTS 4,440,617   4/1984   Solomon ..................... 204/290 R
4,730,109   3/1988   Afromowitz ..................... 250/226

OTHER PUBLICATIONS

Gal et al., "Novel Contactless Electroreflectance Spectroscopy of Semiconductors," Appl. Phys. Lett vol. 56 #6, Feb. 5, 1990 pp. 545–547.
Ginly et al., "Photoelectrochemistry and Electrosynthesis as Semiconductor Materials" Proceedings, vol. 88-14, pp. 468–476.

Primary Examiner—Richard A. Rosenberger
Assistant Examiner—K. P. Hantis
Attorney, Agent, or Firm—Paul M. Craig, Jr.

[57] ABSTRACT

A method and apparatus for a contactless mode of electroreflectance (ER) which utilizes a condenser-like system, of which the front electrode is light transparent, i.e., for instance, consists of a transparent conductive coating on a transparent substrate which is separated from the sample surface by a thin layer of air. With the use of the method and apparatus of this invention, the contactless electroreflectance spectra could be measured at 300K from a number of materials including semi-insulating bulk GaAs, bulk Si, bulk $Hg_{0.75}Cd_{0.25}Te$, a GaAs structure with large uniform electric field and a GaAs/GaAlAs coupled double quantum well.

34 Claims, 10 Drawing Sheets

CONTRACTLESS MODE OF ELECTROREFLECTANCE

This application is a continuation-in-part application of the copending application Ser. No. 07/695,019, now abandoned filed May 3, 1991 and entitled "Contactless Mode of Electroreflectance."

FIELD OF THE INVENTION

The present invention relates to a method for measuring characteristics of semiconductor materials by a contactless mode of electroreflectance and to an apparatus for carrying out the method.

BACKGROUND OF THE INVENTION

Of the many optical methods used to investigate semiconductors and semiconductor microstructures, one of the most useful is electromodulation (EM). In electromodulation, the periodic modulation of an applied electric field produces sharp features in the reflectivity spectrum of the material at photon energies corresponding to interband (intersubband) transitions. These derivative-like resonances can be used to study and characterize many of the important properties of semiconductors (bulk thin film), semiconductor surfaces/interfaces, semiconductor microstructures (single quantum wells, multiple quantum wells, superlattices and heterojunctions) as well as actual device structures.

Electromodulation can be accomplished in several ways, including contact and contactless modes. Four common contact configurations, designated as electroreflectance (ER) can be divided into "longitudinal" and "transverse" categories. The "longitudinal" method can be applied in the semiconductor-electrolyte, metal-insulator-semiconductor, Schottky barrier or PIN configurations. In the latter the sample of interest is placed in the insulating region of a PIN diode. The former is the most widely used form of electroreflectance because of ease of implementation as the sample surface requires no special preparation. However, it can be used only over a limited temperature range (300K to 150K) and often offers less control over the space charge field owing to chemical passivation or dissolution effects. Electrolyte electroreflectance (EER) can be employed for depth profiling measurements with the proper choice of electrolyte and electrochemical conditions. Schottky barrier, metal-insulator-semiconductor and PIN methods can be used at low temperatures to reduce lifetime broadening. The PIN configuration produces a constant electric field as opposed to the position-dependent field of the other "longitudinal" modes. However, the sample must be specially fabricated in order to employ this mode.

In the "transverse" mode, two metal electrodes are evaporated on the surface of the sample and electromodulation is produced by applying a modulated high voltage ($\sim 1$ kV) across the gap ($\sim 1$ mm.). However, this technique can only be used on materials with resistivities greater than about $10^8$ ohm-cm.

Contactless electromodulation can be performed using photoreflectance (PR) or electron-beam electroreflectance (EBER). The method of photoreflectance is not only contactless but requires no special mounting of the sample. It can be used in any transparent medium under a variety of conditions. Modulation of the electric field in the sample is caused by photoexcited electron-hole pairs created by a pump source, such as a laser or other light source, which is chopped at a frequency $\Omega_m$. These photo-injected electron-hole pairs modulate the built-in electric field of the semiconductor or semiconductor microstructure. The photon energy of the pump source must be above the bandgap of the semiconductor being investigated. A typical pump is a 5 mW He-Ne laser, except at high temperatures where a more powerful beam must be used. In electron-beam electroreflectance, the pump beam is replaced by a modulated low energy electron beam ($\sim 200$ eV) chopped at about 1 kHz. However, the sample and electron gun must be placed in an ultra-high vacuum chamber.

Recently, a new version of differential reflectivity has been reported by M. Gal and C. Shwe, Appl. Phys. Lett. 56, 545 (1990) which sometimes contains an electromodulation component. This contactless optical method measures the difference between the reflectivities of two materials (sample/reference). In this approach the sample/reference is mounted so that it performs small oscillations in the plane perpendicular to the incoming probe light beam. If there is a difference in electric field between the sample and reference an electromodulation-like signal can be produced.

SUMMARY OF THE INVENTION

The present invention involves a novel contactless method of electromodulation which utilizes a condenser-like system consisting of a thin, transparent, conductive coating such as, for example, an indium-tin-oxide or about 50-60 Å of a metal such as Au or Ni, on a transparent substrate, such as glass, quartz, etc., which serves as one electrode (capacitor plate). A second electrode (capacitor plate) consisting of a metal strip is provided in the condenser-like system which is separated from the first electrode by insulating spacers. The sample having a thickness of about 0.5 mm. is placed in between these two capacitor plates. The dimensions of the spacer are such that there is a very thin layer of air ($\sim 0.1$ mm) between the front surface of the sample and the conducting part of the first electrode. Thus, there is nothing in direct contact with the front surface of the sample. In the alternative, the one electrode (capacitor plate) as also the second electrode may be replaced with a wire mesh mode of common metals suich as copper. The modulating and bias voltages, the values of which are selected as known to those skilled in the art, are applied between the metal strip and the transparent conductor. Contrary to the metal-insulator-semiconductor configuration, no separate insulator is required as the air (or vacuum) of the gap constitutes an insulator. The probe beam is incident through the first transparent electrode. The method in accordance with the present invention will be referred to hereinafter as contactless electroreflectance because the method is not only contactless but can be used in any transparent medium, including air.

Accordingly, it is an object of the present invention to provide a method and apparatus for a contactless electroreflectance system which avoids by simple means the aforementioned shortcomings and drawbacks encountered with the prior art systems.

Another object of the present invention resides in a method and apparatus for a contactless electroreflectance configuration which is relatively simple in structure and easy to use.

A further object of the present invention resides in a method and apparatus for realizing contactless electroreflectance measurements within a wide range of temperatures.

A still further object of the present invention resides in a method and apparatus for carrying out contactless electroreflectance measurements of the spectra of samples which neither requires a high degree of vacuum nor an electrolytic fluid.

BRIEF DESCRIPTION OF THE DRAWINGS

These and other objects, features and advantages of the present invention will become more apparent from the following description when taken in connection with the accompanying drawing which shows, for purposes of illustration only, one embodiment in accordance with the present invention, and wherein.

DETAILED DESCRIPTION OF THE DRAWINGS

Figure 1:
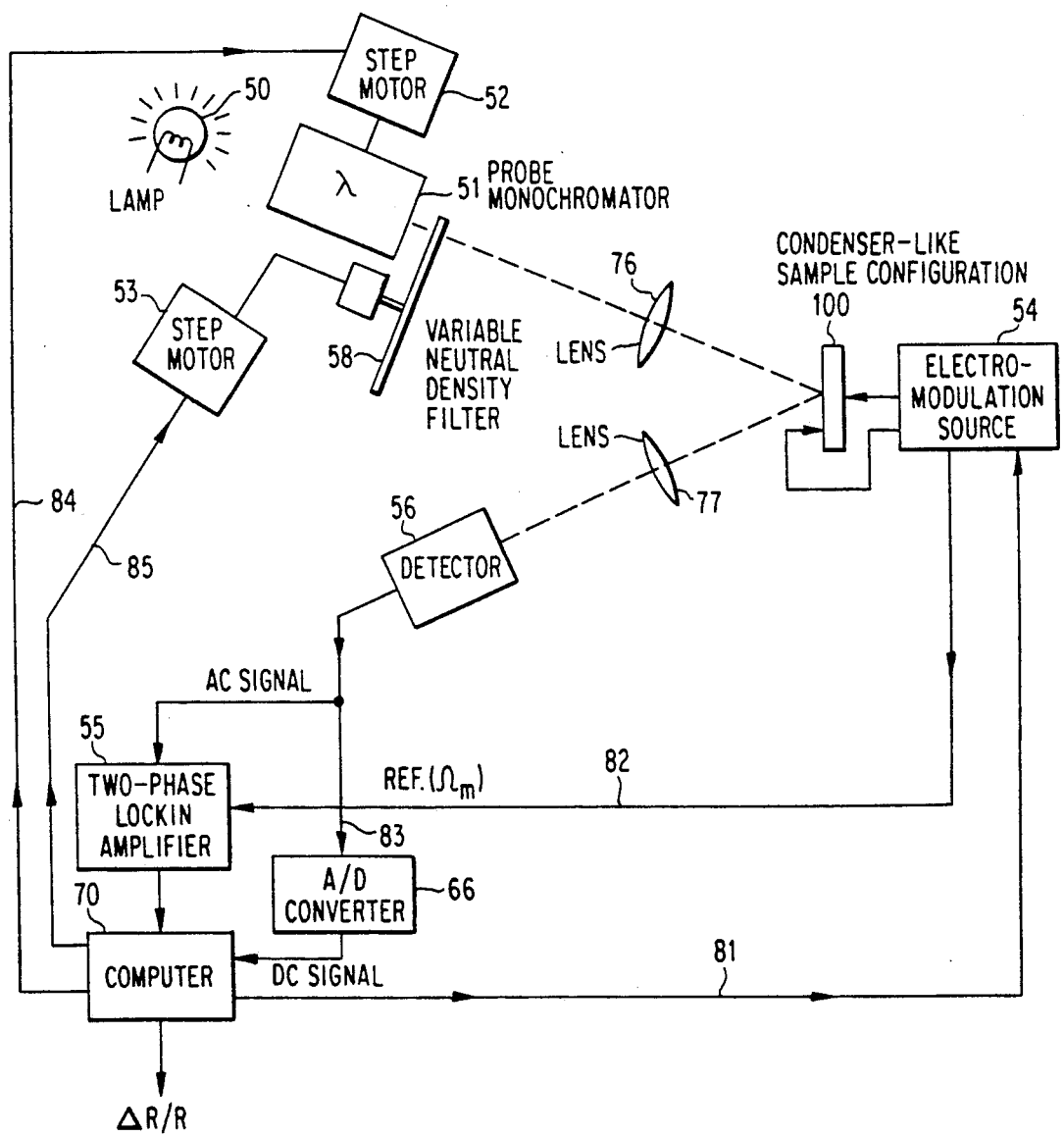
FIG. 1 is a schematic block diagram of an apparatus for a contactless electroreflectance system in accordance with the present invention.

Referring now to the drawing wherein like reference numerals are used in the various vies to designate like parts, and more particularly to FIG. 1, reference numeral 50 designates an appropriate lamp source whose light passes through a monochromator 51, to be referred to hereinafter also as probe monochromator. The exit intensity of the monochromator 51 at the wavelength $\lambda$ is focused onto the condenser-like configuration 100 which contains the sample 62 by means of conventional lenses or mirrors. $I_o(\lambda)$ is thereby the intensity of light from the probe source 50, 51 striking the sample 62. Electromodulation of the sample 62 is produced by the electromodulation source 54 of any known type which provides both an a.c. voltage, for example, of about 1 kV peak-to-peak and a d.c. (bias) voltage. The values of these voltages are chosen on the particular parameters, such as dimensions, materials, etc. as known to those skilled in the art. The beam reflected from the sample 62 is again collected by conventional second lenses 77 or mirrors and is focused on a detector 56, such as a photomultiplier, photodiode, photoconductor, etc. Although FIG. 1 shows the configuration for reflectance, the experiment can also be readily modified for transmission. This is done by placing the detector behind the sample and replacing the second metal electrode with an electrode similar to the first transparent electrode. Accordingly, the term electroreflectance is used in this application in a broad sense to encompass both reflectance and transmittance.

The output of the detector 56 contains two signals, i.e., a d.c. signal and an a.c. signal. The d.c. signal is applied to a computer generally designated by reference numeral 70 by way of A/D converter 66. The a.c. signal from the detector 56 is applied to a lock-in amplifier 55 which also receives a reference signal $\Omega_m$ from the electromodulation source 54 by way of line 82. The desired signal $\Delta R/R$ contained in the output of the lock-in amplifier 55 is applied to computer 70.

The probe monochromator 51 is driven by step-motor 52 which is controlled by the computer 70 of any conventional construction, programmed by conventional techniques to achieve the various functions described herein as also disclosed more fully in the co-pending application Ser. No. 07/408,903, filed Sep. 13, 1989 and entitled "Method and Apparatus for Determining A Material's Characteristics By Photoreflectance Using Improved Computer Control," the subject matter of which is incorporated herein by reference. The variable neutral density filter 58 is driven by a step-motor 53 which is also controlled by the computer 70. It has been found that the signal-to-noise ratio can be improved by a factor of 10 using a step-motor control. In addition, the computer 70 also controls the frequency ($\Omega_m$) of the electromodulation by way of line 81. Furthermore, the lock-in amplifier 55 is a two-phase model of known construction which determines the in-phase and out-of-phase components of the photoreflectance signal (relative to the pump beam). The use of the two-phase lock-in amplifier 55 permits evaluation of the electroreflectance signal as a function of $\Omega_m$ to yield information about trap states. It has also been found that signals from different depth regions of a sample structure produce signals with different phases and dependence on $\Omega_m$ which can be sorted out by the two-phase lock-in amplifier 55 and the computer-controlled modulated frequency $\Omega_m$.

OPERATION

In the operation of the apparatus according to FIG. 1, the probe light produced by lamp 50 in conjunction with the probe monochromator 51, which can be adjusted by step-motor 53 to vary the wavelength $\lambda$ of the probe light, is directed into sample 62 by the use of a lens(es) or mirror(s), schematically indicated in the drawing by lens 76. The electromodulation frequency $\Omega_m$ can be varied by computer 70 by way of line 81. The light reflected (transmitted) from the sample 62 is then directed onto detector 56 by a lens(es) or mirror(s), schematically indicated by lens 77. The a.c. signal in the output of detector 56 is then applied to the input of the two-phase lock-in amplifier 55 to which is also applied a reference signal ($\Omega_m$) from the modulator 54 by way of line 82 to provide information about the modulating frequency $\Omega_m$. The d.c. signal from detector 56 is applied to computer 70 by way of line 83 which includes an A/D converter 66 to change the analog signal from detector 56 into a digital signal for use by the computer 70.

Normalization of the electroreflectance signal can also be accomplished without the variable neutral density filter 58 and stepper motor 53 by simply dividing the a.c. signal by the d.c. signal.

One output of computer 70 contains the desired electroreflectance signal $\Delta R/R$ which can be applied to user-friendly displays, e.g. a display screen (not shown) associated with the computer. Another output of computer 70 controls the step-motor 52 to vary the probe-light wavelength $\lambda$, by way of line 84. A further output of computer 70 controls the step-motor 53 to vary the adjustment of the variable neutral-density filter 58 by way of line 85, and still another output of computer 70 controls the frequency $\Omega_m$ of the modulator 54 by way of line 81.

Figure 2:
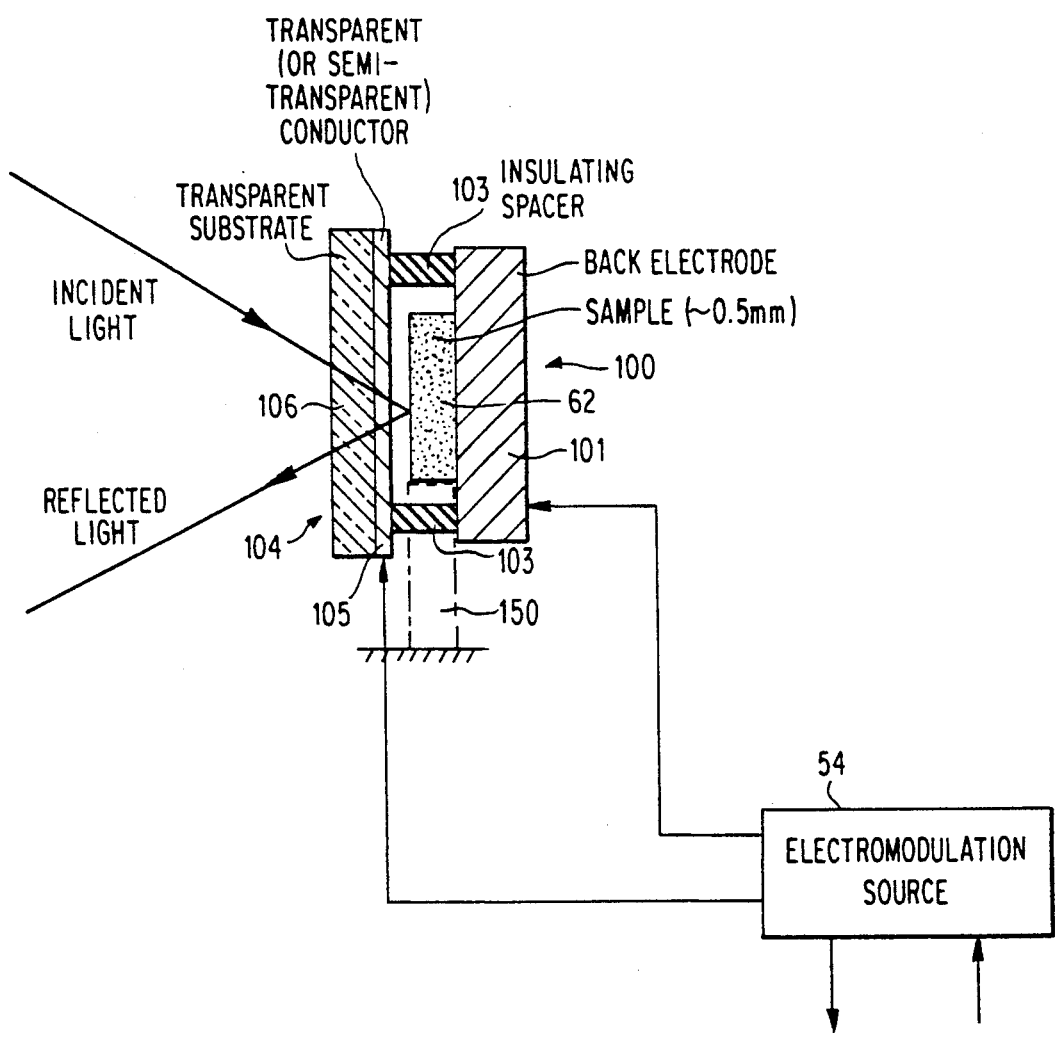
FIG. 2 is a schematic view, on an enlarged scale, of the condenser-like arrangement used in the system of FIG. 1.

FIG. 2 illustrates schematically the "condenser"-like configuration generally designated by reference numeral 100 which is used in the contactless electroreflectance system of the present invention. The back electrode 101 is a metal strip. The sample 62, which is typically 0.5 mm. thick, is placed against the metal electrode 101. The insulating spacers 103 are typically about 0.05-0.1 mm. thicker than the sample 62. The front electrode generally designated by reference numeral 104 consists of a transparent (or semi-transparent) conductor 105 on a transparent substrate 106. The conductor 105 can be indium-tin-oxide or 50-60 Å of a metal such as Au or Ni. The conductor 105 faces the front surface of the sample 62. The front electrode 104 thereby does not touch the surface of the sample 62. The sample 62 is held in place by any conventional means, not forming part of the present invention, and known as such to persons skilled in the art of semi-conductor techniques in which conventional holding devices are used to hold in place, for example, wafers or chips in manufacturing and testing equipments. For that reason, the holding means for the sample 62, which may support the sample along a lateral edge or edges, are shown only schematically in FIG. 2, where they are designated by reference numeral 150 and shown to engage a lateral edge of the sample. The a.c. modulating and d.c. bias voltages are applied between the back metal electrode 101 and the transparent conductor 105. For transmission measurements the back metal electrode 101 is replaced by an electrode similar to the transparent front electrode 104.

For topographical scans, the light from lens 76 is focused onto sample configuration 62 to a size of about 100 $\mu$m and the sample configuration is mounted on an X-Y stage of conventional construction.

Figure 3A:
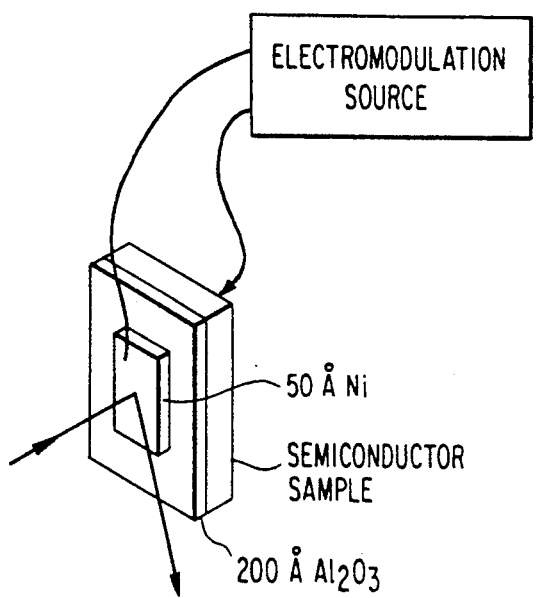
FIGS. 3a, 3b and 3c are schematic illustrations of prior art electroreflectance systems.
Figure 3B:
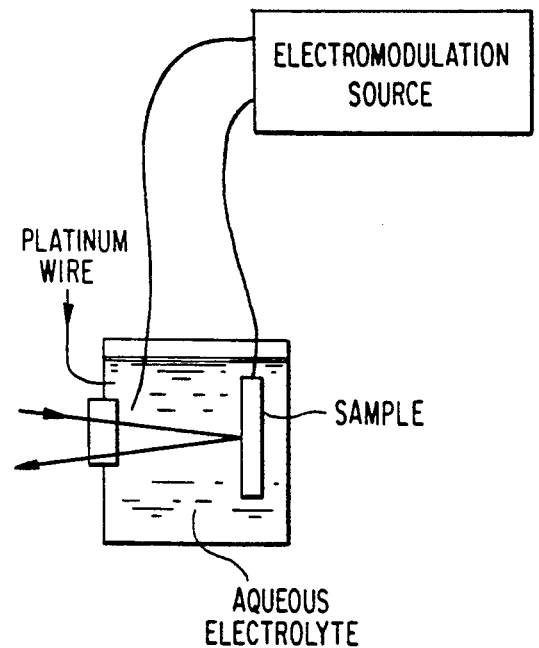
Figure 3C:
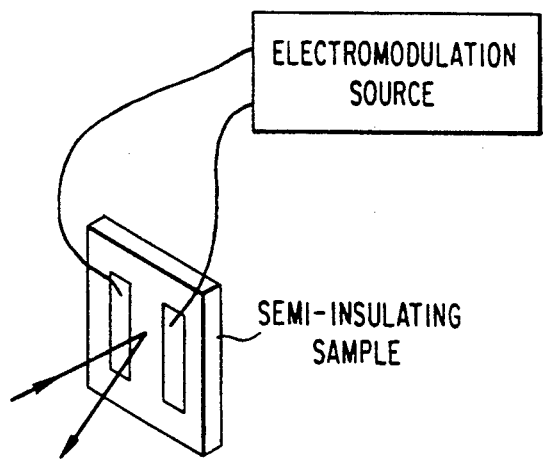

The condenser-like arrangement 100 of FIG. 2 according to the present invention which enables the contactless electroreflectance system together with the distinct advantages described above, differs significantly from the prior art electroreflectance systems which are schematically illustrated in FIGS. 3a, 3b and 3c. FIGS. 3a and 3b thereby illustrate electroreflectance in the metal-insulator-semiconductor and semiconductor/electrolyte configurations, respectively. The metal-insulator-semiconductor configuration of FIG. 3a consists of about 200 Å of an insulator such as Al$_2$O$_3$ onto which has been evaporated about 50 Å of Ni (semi-transparent), while FIG. 3c illustrates a typical transverse configuration of electroreflectance.

Figure 4:
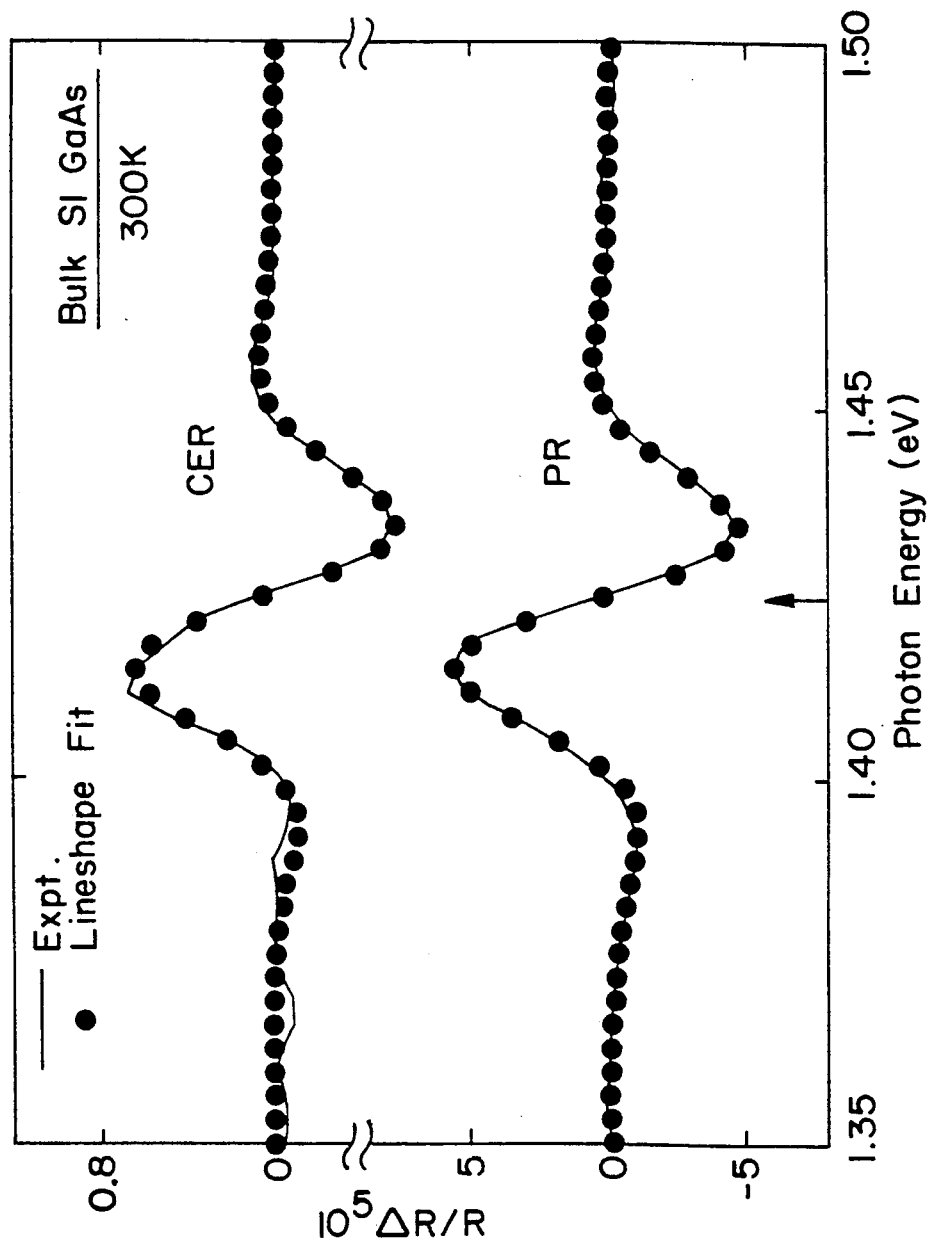
FIG. 4 is a diagram illustrating the contactless electroreflectance and photoreflectance spectra obtained with a semi-insulating (SI) bulk GaAs sample.

The solid lines in FIG. 4 are the contactless electroreflectance (CER) and photoreflectance (PR) spectra at 300K of a sample of polished (001) semi-insulating (SI) bulk GaAs (0.5 mm. thick) grown by the liquid encapsulated Czrochalski method. Such material is frequently used as a substrate to fabricate GaAs, GaAlAs and InGaAs semiconductor microstructures. The photoreflectance data were taken with the Brooklyn College photoreflectance apparatus using a 3 mW He-Ne laser chopped at 200 Hz as the pump source. The contactless electroreflectance (CER) measurements were taken with the apparatus of FIGS. 1 and 2 according to this invention, using a modulating voltage of 500 V at 200 Hz. The spectra are in the range of the fundamental band gap ($E_o$) of GaAs. The solid lines are least-squares fits to a first-derivative Gaussian lineshape function. The obtained energy 1.424 eV for $E_o$ is indicated by the arrow at the bottom of FIG. 4. The first-derivative Gaussian lineshape profile is appropriate for electromodulation of an exciton associated with $E_o$. It is also noted that the two spectra are almost identical. Since photoreflectance produces electromodulation, this comparison demonstrates that the contactless electroreflectance of this invention also is an electromodulation method.

Figure 5:
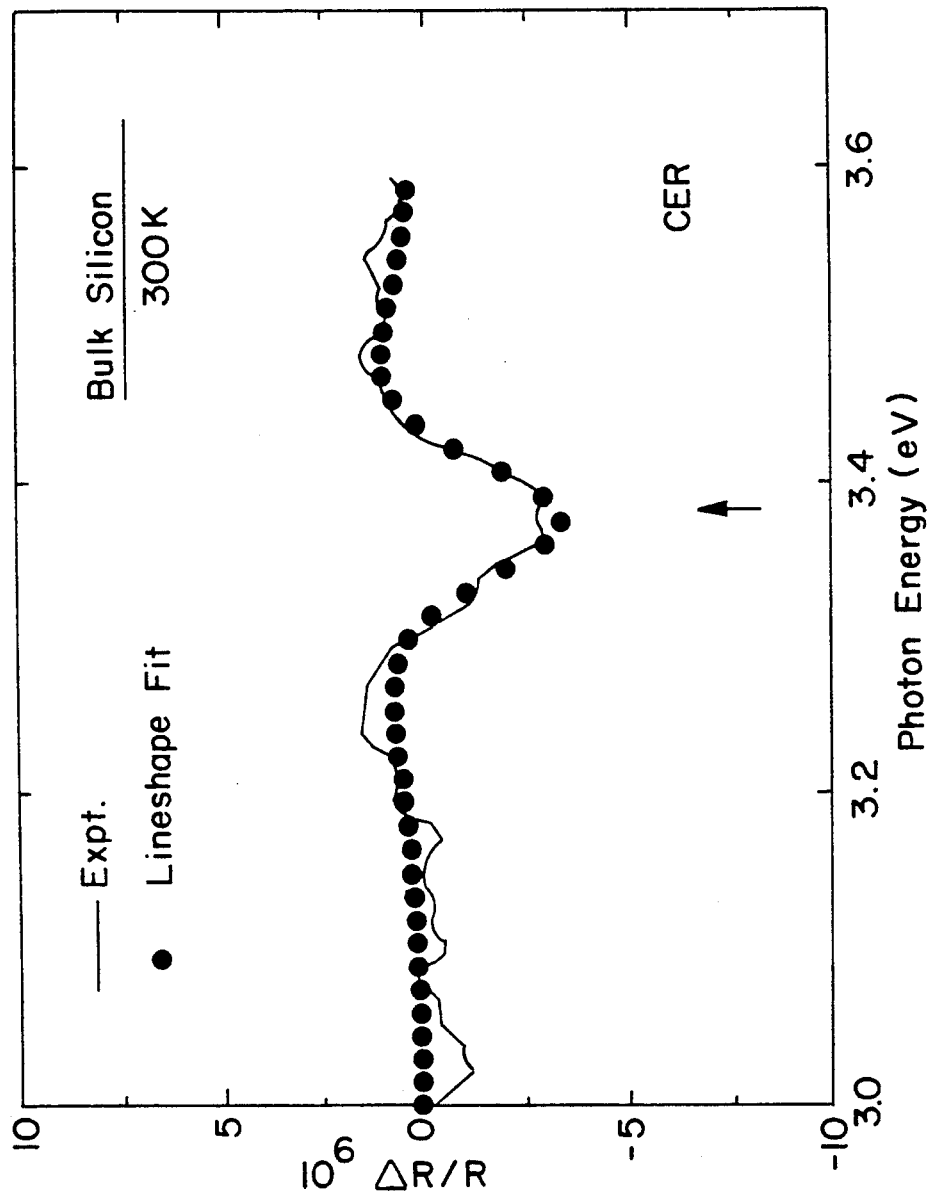
FIG. 5 is a diagram illustrating a contactless electroreflectance spectrum of a sample of bulk Si obtained in accordance with the present invention.

In FIG. 5 is plotted the contactless electroreflectance spectrum at 300K of a sample of bulk Si in the region of the $E_1$ optical feature. It was not possible to obtain a photoreflectance signal form this material. The dashed line is a least-squares fit to the two-dimensional critical point appropriate to the $E_1$ feature which is due to transitions along the <111> direction of the Brillouin zone. The obtained energy gap is denoted by an arrow at the bottom of FIG. 5.

Figure 6:
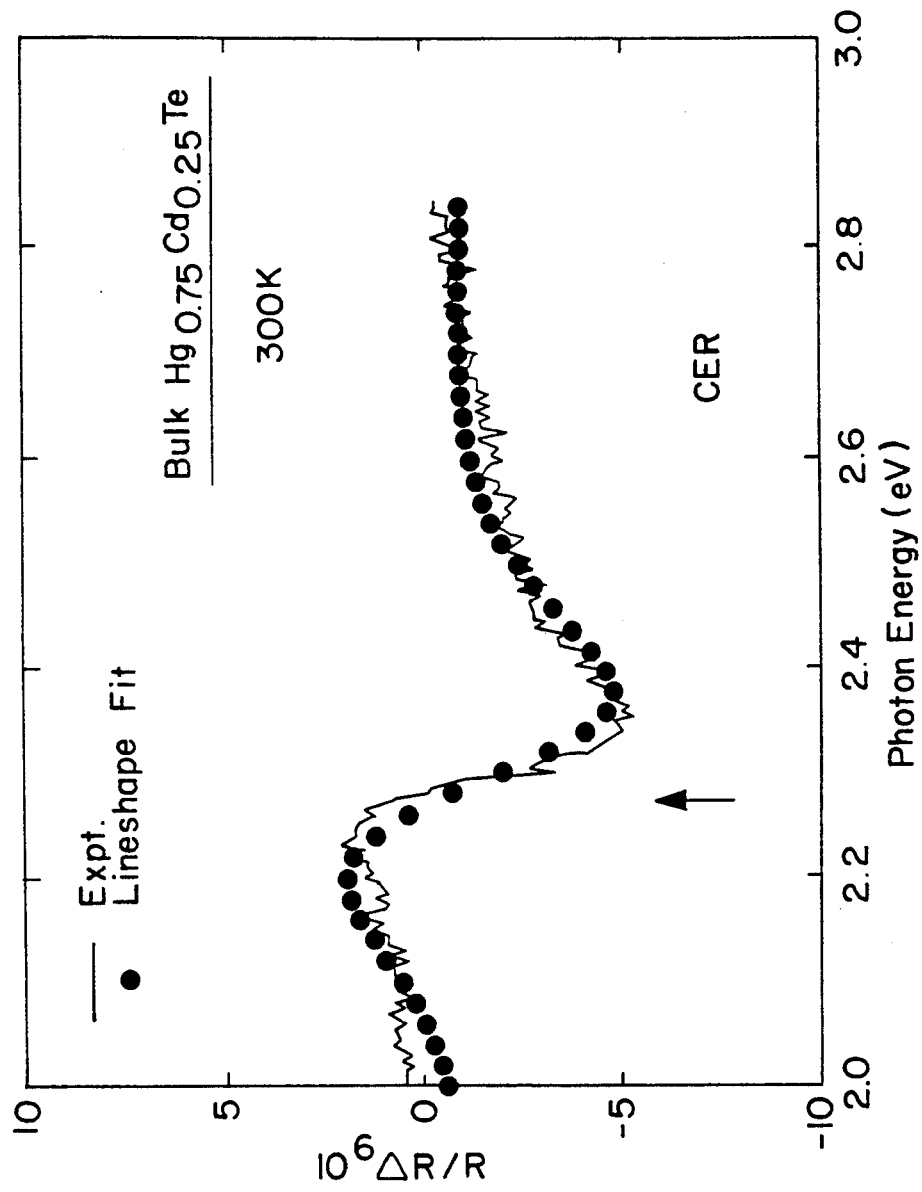
FIG. 6 is a diagram illustrating the contactless electroreflectance spectrum of a bulk $Hg_{0.75}Cd_{0.25}Te$ sample obtained in accordance with the present invention.

The contactless electroreflectance spectrum of a bulk Hg$_{0.75}$Cd$_{0.25}$Te at 300K in the range of the $E_1$ feature is displayed in FIG. 6. No photoreflectance signal at 300K could be obtained from this sample. The solid line is a least-squares fit to a two-dimensional critical point. The obtained energy gap is indicated at the bottom of FIG. 6. This energy enables the determination of the Hg composition. These results are extremely significance since in the past it has not been possible to obtain signals from Hg$_x$Cd$_{1-x}$Te ($X \approx 0.2$-$0.3$) at 300K using other contactless electromodulation methods such as photoreflectance or electron beam electroreflectance. These experimental techniques have yielded signals only at 77K or below. The material Hg$_x$Cd$_{1-x}$Te ($X \approx 0.2$-$0.3$) is extremely useful for infrared detectors.

Figure 7:
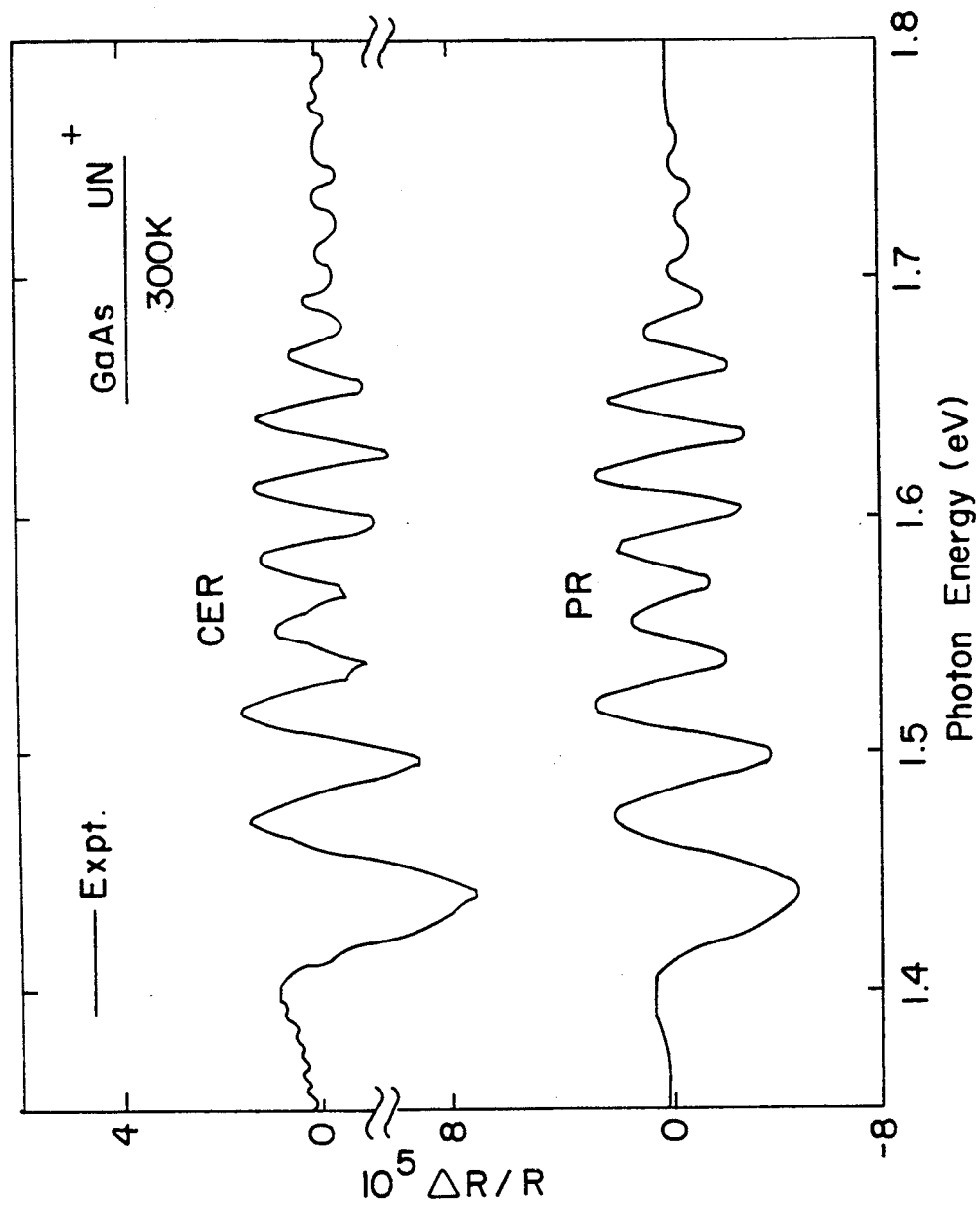
FIG. 7 is a diagram illustrating the contactless electroreflectance and photoreflectance spectra from a GaAs sample with a large, uniform built-in electric field.

The contactless electroreflectance and photoreflectance spectra from GaAs with a large, uniform electric field are shown in FIG. 7. It should be noted that the two spectra are almost identical. The signals exhibit a large number of Franz-Keldysh oscillations which can be used to evaluate the built-in electric field and hence the Fermi level pinning value. This GaAs structure was prepared by molecular beam epitaxy by fabricating an undoped layer of thickness L($=110$ mm.) on a buried 1 $\mu$m Si-doped GaAs buffer (n$\sim 2 \times 10^{18}$cm$^{-3}$) on an n+ substrate. Such a configuration is designated as UN+. Because of Fermi level pinning at the surface, there exists an almost uniform field F in the undoped layer.

Figure 8:
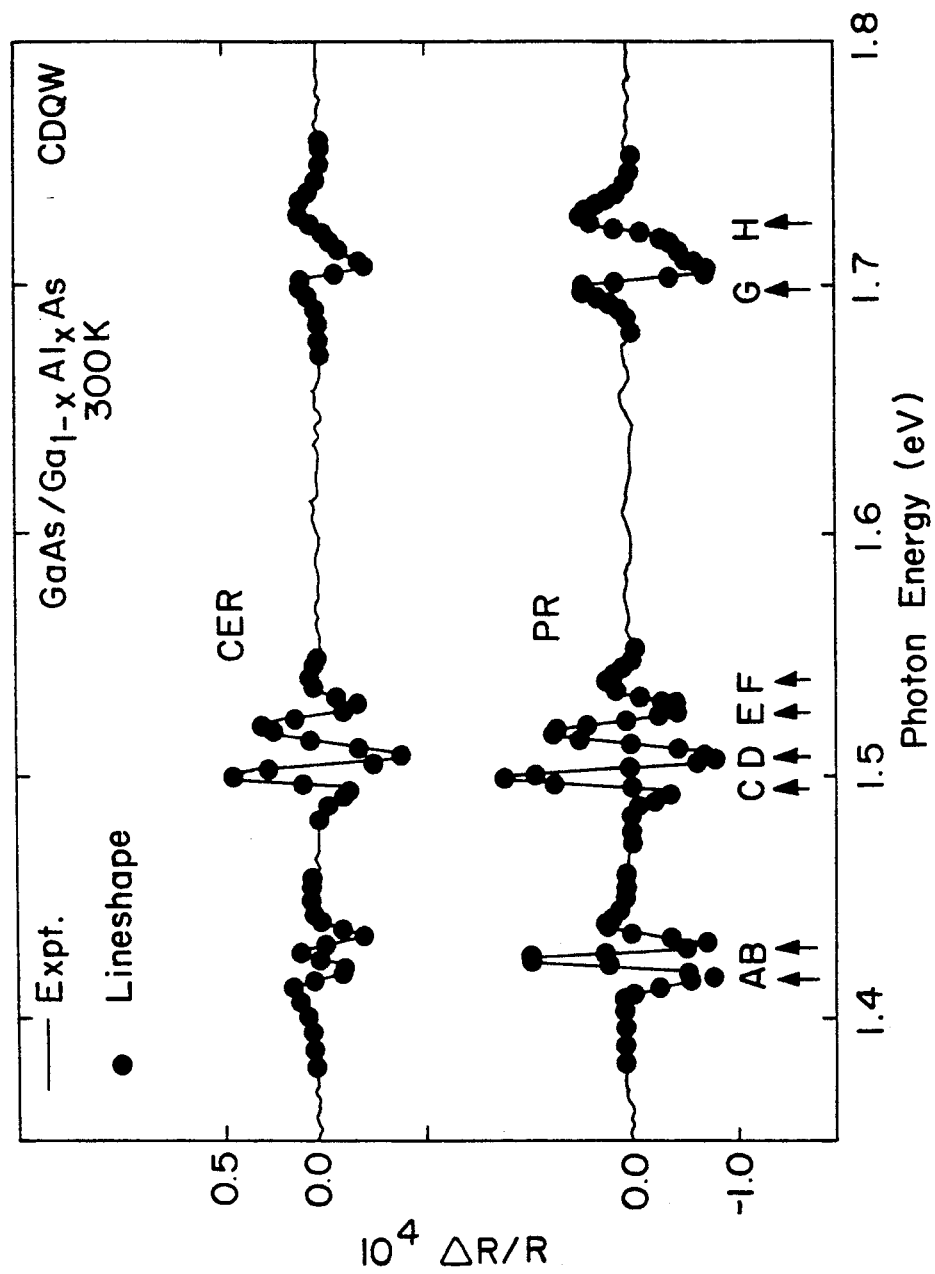
FIG. 8 is a diagram illustrating the contactless electroreflectance and photoreflectance signals obtained from a GaAs/GaAlAs coupled double quantum well sample.

The contactless electroreflectance and photoreflectance signals from a GaAs/GA$_{1-x}$Al$_x$As coupled double quantum well is shown in FIG. 8. The structure consisted of a 1 $\mu$m GaAs buffer grown by MBE on an SI (001) GaAs substrate. This was followed by 1000 Å of Ga$_{1-x}$Al$_x$As. The coupled double quantum well consisted of two 60 Å GaAs quantum wells separated by 40 Å of Ga$_{1-x}$Al$_x$As. On top of this was grown 300

Å of $Ga_{1-x}Al_xAs$ followed by a 100 Å cap of GaAs. Again the similarity of the two spectra are significant. The dashed lines are least-squares fits to appropriate electromodulation lineshape functions. The obtained energies are indicated by arrows at the bottom of FIG. 8. The peaks labelled A and B correspond to the energy of $E_o$ of GaAs and originate in the GaAs buffer/substrate. The features denoted by arrows C, D, E and F are due to transitions in the coupled double quantum well. The structures C and E are related to the symmetric and anti-symmetric components of the fundamental conduction to heavy-hole transitions. The peaks D and F are the counterparts for the fundamental conduction to light-hole transitions. The peaks G and H originate in the $Ga_{1-x}Al_xAs$ portion of the sample. The former corresponds to an Al composition of 19% while the latter denotes an Al content of 21%. Thus, the various $GA_{1-x}Al_xAs$ regions do not have the same composition.

Figure 2A:
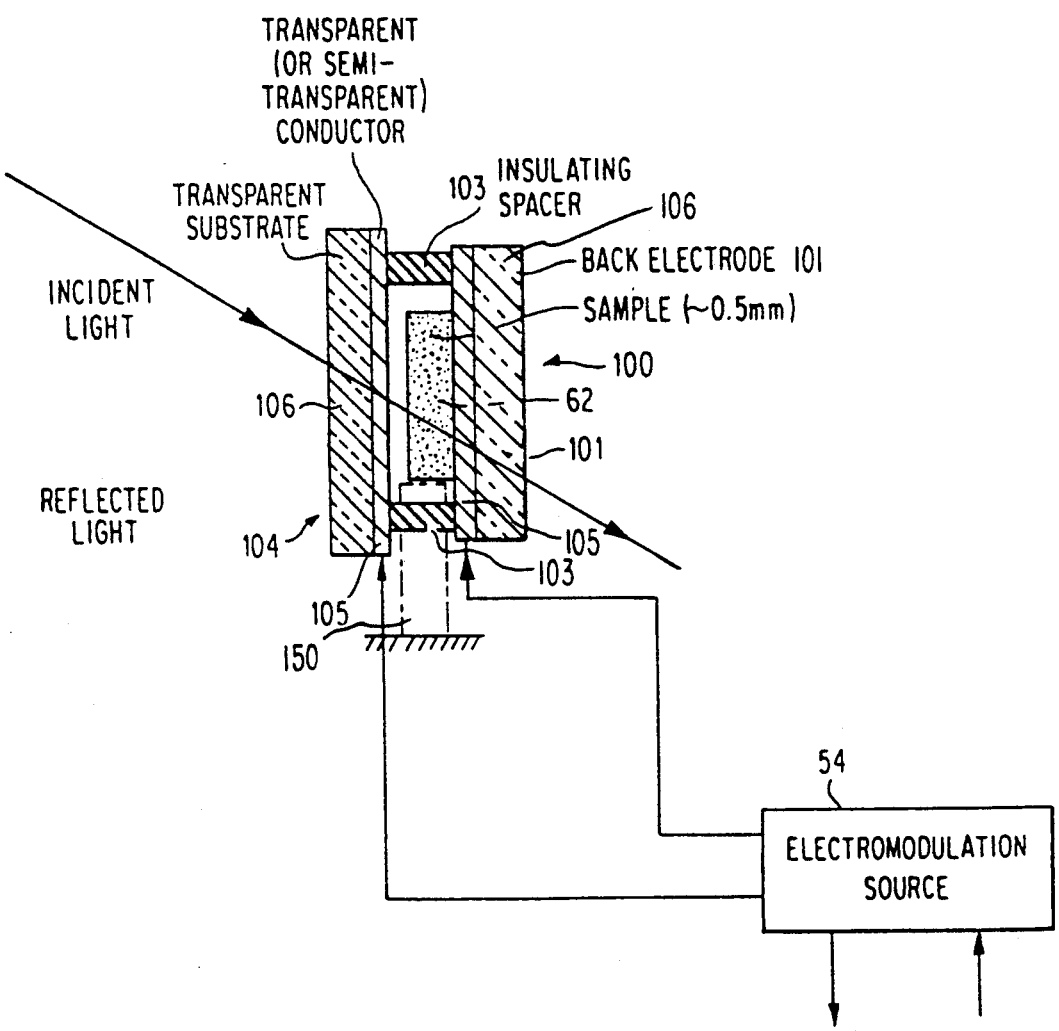
FIG. 2A is a schematic view, on an enlarged scale, of a modified condenser-like arrangement for use in a system in which measurements are made in connection with a signal transmitted through the sample.
Figure 9:
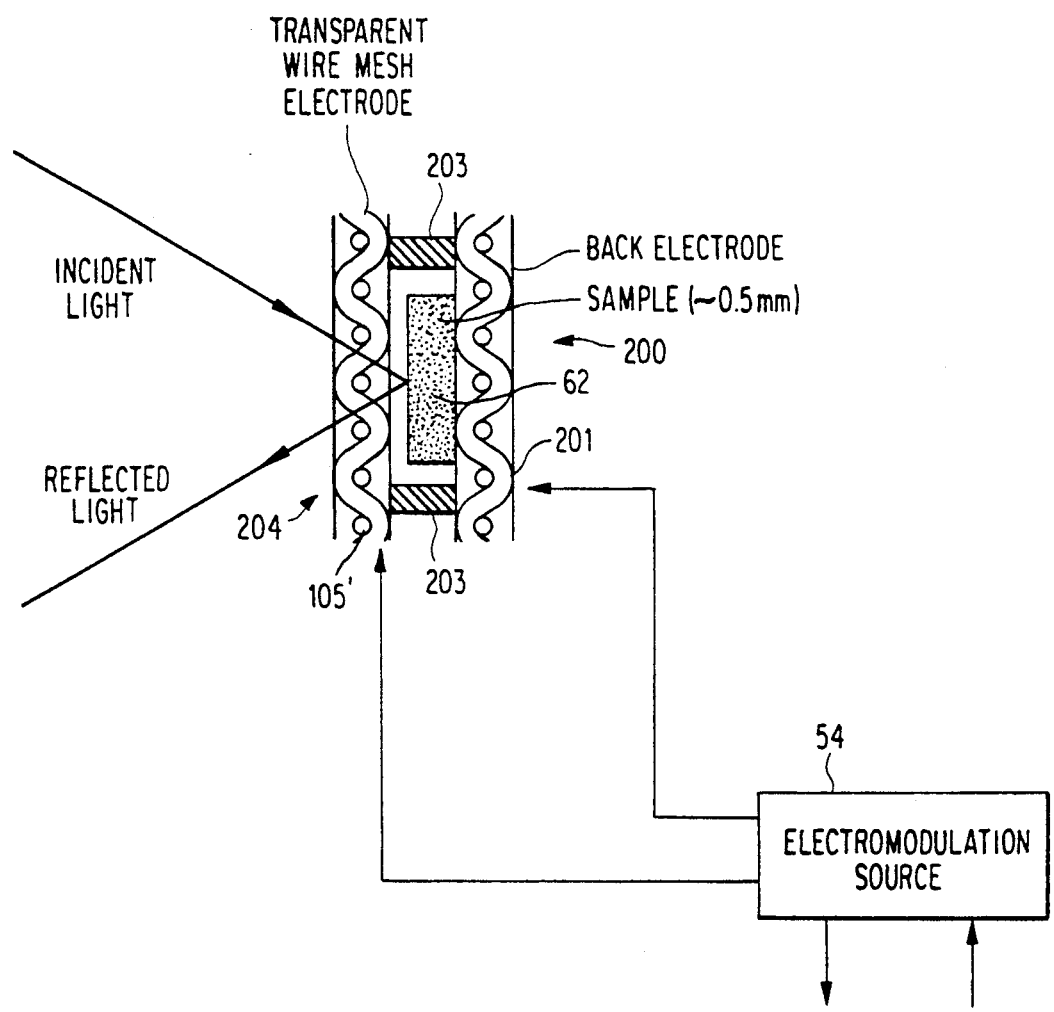
FIG. 9 is a schematic view, on an enlarged scale and similar to FIG. 2, of a modified condenser-like arrangement utilizeable in the system of FIG. 1.

Referring now to the modified embodiment of FIG. 9 in which corresponding elements are designated by reference numerals of the 200 series, the condenser-like configuration of this modified embodiment differs from that of FIG. 2 in that the front electrode generally designated by reference numeral 204 is now formed by a wire mesh electrode replacing the transparent conductor 105 and transparent substrate 106 of the embodiment of FIG. 2. For purposes of measurement signals transmitted through the sample, the back electrode 201 can also be replaced by a wire mesh in a manner analogous to the replacement of the back electrode as shown in FIG. 2A. The wire mesh may be a conventional commercially available wire mesh structure having a grid dimension of about 2 mm.×2 mm. between the wires. The wire mesh may be made of common metals such as copper and may be of the type commercially available, for example, in hardware stores where such wire mesh is used as a screen. The wire mesh has the advantage that it is completely transparent. In general, the "transparent" conductor 105, "transparent" substrate 106 are transparent only over a certain wavelength region. For example, indium tin oxide becomes opaque for wavelengths shorter than about 3,500 Å. Also utilizing the wire mesh electrode, it will be possible to realize measurements up to elevated temperatures not possible with the substrate 106 which is generally made of glass or quartz.

While we have shown and described only one embodiment in accordance with the present invention, it is understood that the same is not limited thereto but is susceptible of numerous changes and modifications as known to those skilled in the art. For example, it is also possible to so arrange the condenser-like structure that the sample is out of contact with both electrodes whereby the structure of both electrodes can be varied as known to those skilled in the art, i.e., the back electrode may be similar to or different from the front electrode. Furthermore, in the illustrated arrangement according to FIG. 2, the back electrode may also be grounded. We therefore do not wish to be limited to the details shown and described herein but intend to cover all such changes and modifications as are encompassed by the scope of the appended claims.

We claim:

1. An apparatus for obtaining information concerning material characteristics of a sample by contactless electroreflectance, comprising first means forming a condenser-like structure having two electrode means and means for holding a sample out of contact with at least one of said electrode means in such a manner that there is nothing in direct contact with the surface of said sample facing said one electrode means but any surrounding gaseous medium having insulating properties, means for directing a probe beam of light onto the sample through the electrode means located in front of the sample as viewed in the direction of incidence of the probe beam, electromodulation source means operatively connected with said electrode means for applying thereto a modulating voltage, means for detecting the beam upon reflection from, respectively, transmission through the sample, and further means for obtaining a signal from said detector means which contains the information.

2. An apparatus according to claim 1, wherein the two electrode means are spaced from one another by insulating spacer means in such a manner that the sample is out of contact with the electrode means disposed in front thereof.

3. An apparatus according to claim 2, wherein at least the electrode means which is positioned in front of the sample is at least partially transparent.

4. An apparatus according to claim 1, wherein said sample is in contact with the electrode means disposed to the rear thereof.

5. An apparatus according to claim 1, wherein the sample is out of contact also with both electrode means.

6. An apparatus according to claim 3, wherein the last-mentioned electrode means includes a substantially transparent substrate with an at least semi-transparent conducting element on the side thereof facing the sample.

7. An apparatus according to claim 1, wherein electrode means disposed to the rear of the sample is a metallic electrode.

8. An apparatus according to claim 7, wherein said sample is in contact with the electrode means disposed to the rear thereof.

9. An apparatus according to claim 1, wherein the electrode means disposed to the rear of the sample includes a substantially transparent substrate with an at least partially transparent conductor on the side thereof facing the sample.

10. An apparatus according to claim 1, wherein the electrode means disposed in front of the sample is formed by a metallic wire mesh.

11. An apparatus according to claim 10, wherein said wire mesh electrode means has a grid dimension of about 2 mm.×2 mm. between its wires.

12. An apparatus according to claim 11, wherein said wire mesh electrode means is made from copper.

13. An apparatus according to claim 10, wherein the electrode means to the rear of the same is also made from metallic wire mesh.

14. An apparatus according to claim 13, wherein the last-mentioned wire mesh electrode means has a grid dimension of about 2 mm.×2 mm. between its wires.

15. An apparatus according to claim 1, wherein the sample has a thickness of the order of 0.5 mm. and the spacing between the sample and the electrode means in front of the sample is of the order of 0.01 mm.

16. An apparatus according to claim 1, wherein the sample is insulated from the electrode means in front of the sample by air.

17. An apparatus according to claim 2, wherein the sample is insulated from the electrode means in front of the sample by air.

18. An apparatus according to claim 17 wherein the sample has a thickness of the order of 0.5 mm. and the spacing between the sample and the electrode means in front of the sample is of the order of 0.01 mm.

19. An apparatus according to claim 18, wherein at least the electrode means which is positioned in front of the sample is at least partially transparent.

20. An apparatus according to claim 1, wherein the means for directing a probe beam onto the sample includes a light source and a probe monochromator associated with the light source for producing a probe beam of predetermined wavelength.

21. An apparatus according to claim 20, wherein the signals from said detector means include both a.c. and d.c. signals, wherein said further means includes computer means, the d.c. signals being applied to said computer means by way of an analog/digital converter and the a.c. signals being applied from said detector means to said computer means by way of a two-phase lock-in amplifier means.

22. An apparatus according to claim 21, wherein said computer means is operable to control the modulating frequency of the electromodulation source means and wherein a signal corresponding to the modulating frequency is fed back from the electromodulation source means to the lock-in amplifier means.

23. An apparatus for obtaining information concerning material characteristics of a sample by contactless electroreflectance, comprising first means forming a condenser-like structure having two electrode means and means for holding a sample out of contact with at least one of said electrode means in such a manner that there is nothing in direct contact with the surface of said sample facing said one electrode means but air or a vacuum having insulating properties, means for directing a probe beam of light onto the sample through the electrode means located in front of the sample as viewed in the direction of incidence of the probe beam, electromodulation source means operatively connected with said electrode means for applying thereto a modulating voltage, means for detecting the beam upon reflection from, respectively, transmission through the sample, and further means for obtaining a signal from said detector means which contains the information.

24. An apparatus according to claim 21, wherein said computer means is operable to control the frequency of the monochromator.

25. An apparatus according to claim 24, wherein said computer means is operable to control a variable neutral density filter placed in front of the monochromator to control the light intensity.

26. An apparatus according to claim 25, further comprising step motor means operatively connected with respective outputs of the computer means to control the monochromator and variable neutral density filter.

27. A method for carrying out measurements by contactless electroreflectance for determining the characteristics in a sample made from a material, such as a semiconductor material, comprising the steps of placing a sample of the material within a condenser-like structure having two electrodes in such a manner that the sample is out of contact with at least one of the electrodes thereof and its surface of said sample facing said one electrode is exposed only to any surrounding gaseous medium having insulting properties, directing a probe beam of light onto the sample through one of the electrodes, subjecting the sample to an electromodulated electric field by applying a modulating voltage from an electromodulating source across the electrodes of the condenser-like structure, detecting by means of a detector the light reflected from, respectively, transmitted through the sample subjected to the modulated electric field, and deriving from detected signals desired signals containing the information indicative of the characteristics of the material.

28. A method according to claim 27, further comprising the step of controlling the modulating frequency at which the electric field is modulated.

29. A method according to claim 27, wherein the detected signals contain a.c. and d.c. components, further comprising the step of determining the in- and out-of-phase components in the a.c. signal components.

30. A method according to claim 29, further comprising the step of feeding back a signal from the electromodulating source for purposes of comparing the in- and out-of-phase components.

31. A method according to claim 27, wherein the detected signals contain a d.c. component, further comprising the step of controlling the light intensity of the probe beam so as to maintain substantially constant the d.c. component in the detected signals.

32. A method according to claim 27, further comprising the step of obtaining for said probe beam a monochromatic probe beam directed onto the sample, and controlling the wavelength of the monochromatic probe beam.

33. A method according to claim 28, wherein the detected signals contain a d.c. component, comprising the step of controlling the modulating frequency of the electromodulating source as also the wavelength of the monochromatic probe beam from a computer to which is fed the d.c. signals from the detector converted into digital signals.

34. A method according to claim 33, further comprising the step of controlling the light intensity of the probe beam from the computer.

* * * * *